United States Patent [19]

Higgins et al.

[11] Patent Number: 5,984,493
[45] Date of Patent: Nov. 16, 1999

[54] ILLUMINATION SYSTEM AND METHOD

[75] Inventors: Frank P. Higgins, Ewing; William Thomas Kenny, Stockton, both of N.J.

[73] Assignee: Lucent Technologies Inc., Murray Hill, N.J.

[21] Appl. No.: 08/839,481

[22] Filed: Apr. 14, 1997

[51] Int. Cl.⁶ .................................................. F21V 21/30
[52] U.S. Cl. ........................... 362/283; 362/18; 362/268; 362/284
[58] Field of Search .................................... 359/385, 387, 359/389, 390; 362/11, 17, 18, 33, 35, 138, 139, 277, 280–284, 268; 356/394

[56] References Cited

U.S. PATENT DOCUMENTS

| | | | |
|---|---|---|---|
| 2,144,653 | 1/1939 | Graff | 359/390 |
| 2,183,462 | 12/1939 | Mestre | 362/33 |
| 3,186,296 | 6/1965 | Erban | 359/390 |
| 3,928,842 | 12/1975 | Green et al. | 356/394 |
| 4,200,396 | 4/1980 | Kleinknecht et al. | 356/394 |
| 4,619,508 | 10/1986 | Shibuya et al. | 362/268 |
| 4,741,621 | 5/1988 | Taft et al. | 356/394 |
| 4,769,743 | 9/1988 | Callahan | 362/18 |
| 4,813,588 | 3/1989 | Srivastava et al. | 359/385 |
| 4,843,529 | 6/1989 | Izenour | 362/268 |
| 4,978,224 | 12/1990 | Kishimoto et al. | 356/394 |
| 5,303,125 | 4/1994 | Miller | 362/277 |

*Primary Examiner*—Alan Cariaso

[57] ABSTRACT

An apparatus for selective multi-directional illumination of an object, particularly for selective multi-directional imaging of an object, comprises a central mirror selectively rotatable about a central axis for reflecting light arriving along the central axis in selected directions radial to the axis. A plurality of differently tilted mirrors are mounted on an annular member selectively rotatable around the central axis for disposing selected ones of the tilted mirrors in the path of light from the central mirror. The tilted mirrors reflect light onto an object at a direction determined by the angular position of the central mirror and at an angle of elevation determined by the selected tilted mirror. Light reflected from the illuminated object reaches an imaging device along a path retracing the illuminating light whereby the direction of viewing of the imaged object corresponds to the direction of illumination of the object.

9 Claims, 5 Drawing Sheets

ILLUMINATION SYSTEM AND METHOD

BACKGROUND OF THE INVENTION

This invention relates, in general, to the illumination of objects, and particularly to multi-directional illumination of objects for multi-directional visual inspection thereof.

A problem in the manufacture of many articles or "objects", particularly small objects, is the need to visually inspect each object from many different directions. A known practice is to view small objects through a microscope with the viewer manipulating the object within the microscope field of view for multi-directional viewing of the object. Microscope viewing, however, tends to be tiring, and a preferred approach is to view small objects with an imaging device, e.g., a TV camera, and to inspect electronically recreated, and preferably magnified, images of the objects. The need remains, however, for multi-directional viewing for a complete visual inspection. Such multi-directional viewing can be achieved by rotating (preferably automatically) each object within the field of view of the camera or by viewing the object from various directions using multiple cameras or one or more movable cameras. With any such approach, the known inspection systems tend to be complex, slow in operation and expensive.

SUMMARY OF THE INVENTION

An illumination system comprises an object receiving station including a reference surface, a first and (optionally) a second source of illumination ("light", hereinafter), and first and second mirror assemblies for directing light from the first light source onto the object receiving station from selected different directions around the periphery of the station and at selected different angles of elevation relative to the reference surface. In a preferred embodiment, the system is used with an imaging device for imaging an object on the station from different directions and angles as determined by the multi-directional illumination of the object.

The first mirror assembly comprises a plurality of first mirrors, preferably individual, spaced apart mirrors or a single adjustable first mirror, each for reflecting light directed thereon onto the object receiving station at a preselected but respectively different angle of elevation relative to the reference surface.

The second mirror assembly comprises a (preferably) single, second mirror for receipt of light from the first light source along a first direction and for reflecting the light along a second direction radial to the first direction and onto respective ones of the first mirrors selectively disposed along the second direction.

A preferred method of operation of the system comprises disposing one of the first mirrors in the path (second direction) of light from the second mirror for directing light onto the object receiving station at a preselected first angle of elevation relative to the station reference surface and from a preselected first direction from the periphery of the receiving station. Some of the light reflected from an object on the receiving station retraces the path of the illuminating light to the first mirror, thence to the second mirror, and thence along the first direction to (e.g., via a beam splitter and a lens system) the imaging device for capturing a view of the object as seen from the first direction and at the first angle of elevation.

Then, either the direction of peripheral viewing of the object or the angle of elevation at which the object is viewed is changed and this new view of the object is captured by the imaging device.

The direction of peripheral viewing of the object (at a fixed angle of elevation) is changed by rotating both mirror assemblies as a single unit and in fixed angular relationship for rotating the second direction path of light from the second mirror relative to the periphery of the object receiving station. The object is thus viewed from different peripheral directions but at the same angle of elevation. The angle of elevation at which the object is viewed is changed by, with the second mirror in fixed angular orientation, placing another first mirror in the path of light from the second mirror. The object is thus viewed at different angles of elevation from the same peripheral direction.

Accordingly, the object can be viewed from each of several peripheral directions at each of several angles of elevation.

Optionally, a second source of light can be directed directly onto the object receiving station for a fixed direction illumination of the station but a multi-directional viewing of the object dependent upon the selected orientation of the two mirror assemblies for directing light reflected from the station to the imaging device.

DESCRIPTION OF THE DRAWINGS

The drawings are not necessarily to scale.

DESCRIPTION OF PREFERRED EMBODIMENTS

Figure 1:
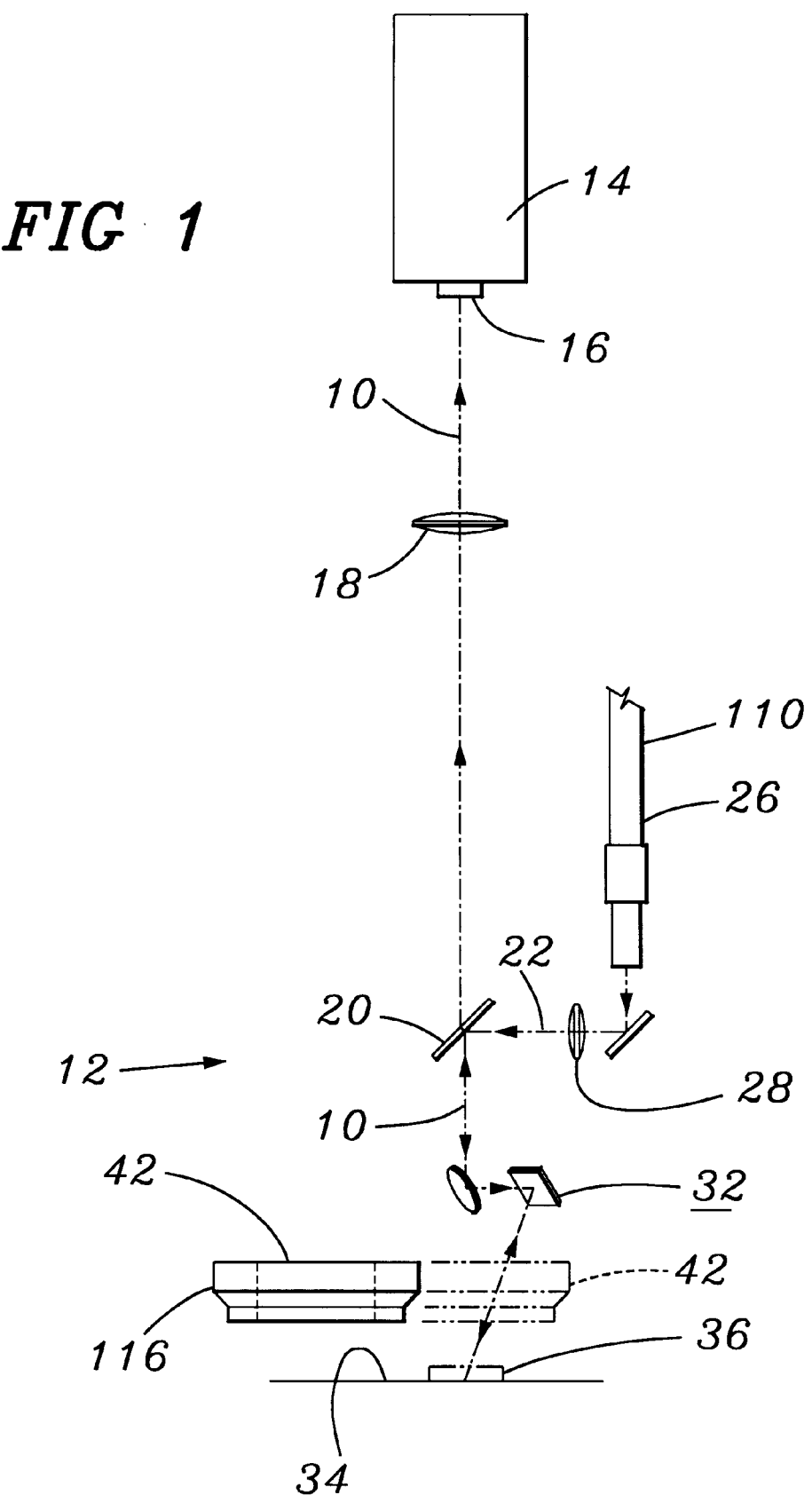
FIG. 1 is a schematic side elevational view of an apparatus according to the invention.
Figure 2:
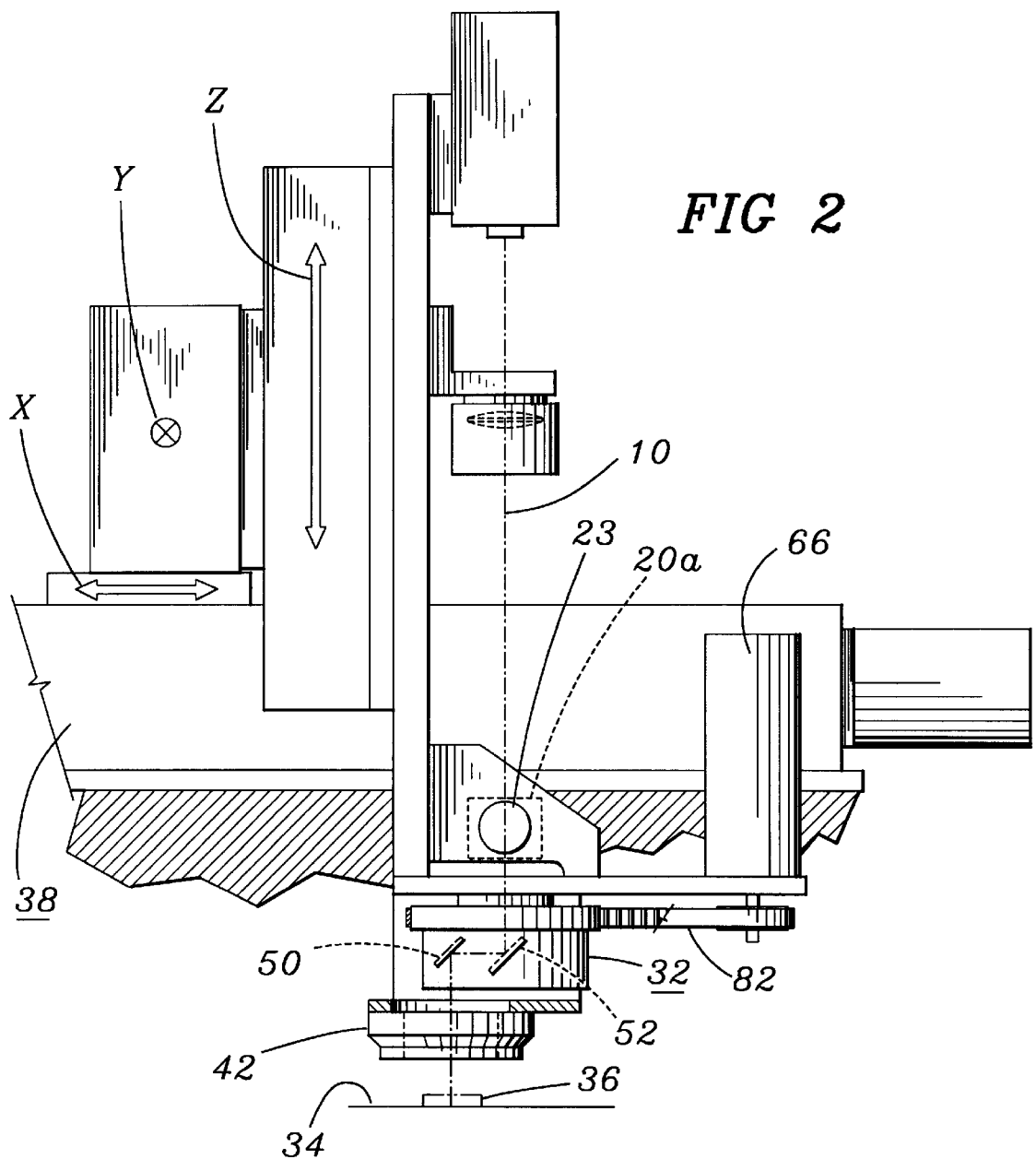
FIG. 2 is similar to FIG. 1, but somewhat more detailed and viewing the apparatus 90 degrees from the FIG. 1 view.

Over-all views of one embodiment of the invention are shown in FIGS. 1 and 2. Both figures are schematic, but with FIG. 2 showing somewhat more structure than FIG. 1, and the view of the apparatus in FIG. 2 being at 90 degrees from the view in FIG. 1. It is convenient to refer to a central axis 10 of the inventive apparatus 12. Principal components of the apparatus 12 are an imaging device 14, e.g., a known type of TV camera, having a light receiving aperture 16 intercepted by the central axis 10, and a focusing lens system 18 of known type for providing proper focusing of the TV camera. Disposed beneath the lens system 18 and on the central axis 10 is a beam splitter 20 (functionally shown in FIG. 1, and disposed in a housing 20a in FIG. 2) of known type which both transmits and reflects light incident upon the beam splitter from along the central axis 10 and from along an axis 22 at right angles to the axis 10. (In FIG. 2, the axis 22 is normal to the plane of the drawing and enters the housing 20a through an aperture 23.)

A first source 26 of illumination (shown only in FIG. 1), is disposed to one side of the central axis 10 for directing a beam of light (through a lens 28) along the axis 22 to the beam splitter 20. In this embodiment, the light source is a known "quartz halogen" bulb which produces light over the full visible frequency range and into the infrared range. Depending upon the articles being inspected and the imaging system used, other radiation frequencies can be used.

Herein, and in the claims, the term "light" is used to denote any illuminating radiation whether in the "visible" light range or not.

The light from the source is directed downwardly along the central axis 10 to a mirror system 32 for directing the light from the beam splitter 20 onto an object receiving station 34 disposed beneath the mirror system. In this embodiment, the apparatus 12 is for visually inspecting articles of manufacture, e.g., semiconductor devices, and conveyor means of known type (not illustrated) are used for sequentially conveying and locating articles to be inspected at the receiving station 34. Herein, the receiving station 34 is indicated by a straight line corresponding to the upper surface of a table or fixture or the like for receipt of the article to be visually inspected, and such article 36 is shown in phantom.

The article 36 has three dimensions, and for the purpose of focusing on various features of the article spaced apart in the three dimensions, the entire apparatus is mounted on a known X–Y–Z translating table 38 (FIG. 2) whereby, under control of a computer, once an article has arrived at the receiving station and, optionally, while the article is being moved along the receiving station surface 34, the entire apparatus is sequentially indexed for bringing successive spaced apart features of the article into the field of focus of the TV camera. In FIG. 2, known mechanisms for causing indexing of the table 38 in each of three mutually perpendicular directions, X, Y and Z are indicated by directional arrows X, Y and Z. Alternately, the table 38 can be stationary, and known mechanisms can be used for indexing the receiving station 34 for proper focusing.

In a preferred use of the apparatus 12, as part of a manufacturing process, a known article is to be inspected and, based upon experiments, a sequence of inspection steps for viewing different parts of the object from different directions and at different angles of elevation is established. This sequence is therefore identically repeated as part of the manufacturing process, and all "parameters" of the inspection process are thus known and programmed.

Computer guided optical-mechanical systems for focusing a camera onto successive volumes of space, particularly where the locations of the volumes are known in advance, are known and not described herein. Novel aspects of the present invention relate to providing illumination of such successive volumes by light arriving from different directions for allowing viewing and imaging of the volumes from different preselected directions. Additionally, different sources of illumination can be used, e.g., a ring light 42 shown in FIGS. 1 and 2 disposed to one side of the apparatus but movable, as desired, to a position shown in phantom in FIG. 1.

The mirror system 32 comprises (FIGS. 3 and 4) two mirror assemblies 44 and 46 (described briefly now and in greater detail hereinafter) mounted for movements (angular indexing) around the central axis 10, both together as a single unit and independently of one another.

A first 44 of the mirror assemblies comprises an annular support 48 (FIG. 3) centered on the central axis 10 and incrementably rotatable around the axis 10. Mounted on the support 48 and facing inwardly thereof are a number of spaced apart "first" mirrors 50. Three mirrors are herein used, but the number is optional dependent upon how the apparatus is to be used. Each mirror 50 is tilted downwardly whereby light incident on the mirrors is reflected downwardly towards the object receiving station 34. Each mirror is disposed at a different angle relative to the central axis 10 whereby each mirror directs light onto the station 34 at a different angle of incidence or (as used herein) angle of elevation, e.g., relative to an axis (such as the central axis 10) normal to the station surface 34. In this embodiment, the three mirrors are disposed at 45, 32 and 27.5 degrees, respectively, to the central axis 10. Accordingly, for light arriving at the three mirrors 50 along directions generally normal to the central axis, the angles of elevation of the light reflected towards the receiving station by the three mirrors are 0, 26 and 35 degrees, respectively.

As described hereinafter, the light incident on the three mirrors 50 is in the form of a circular cone of light (e.g., converging light rays) and each mirror reflects a circular cone of light onto the receiving station. At the receiving station, each mirror 50 thus projects a circular spot of light but with the light spots displaced from each other owing to the different angles of projection of the different light beams. Each light beam from the different mirrors is used separately of the other. Proper positioning of each light spot on a particular preselected portion of an article being inspected, both in terms of centering of the light spot and proper focusing of the camera on the illuminated portion, is achieved by proper positioning of the entire apparatus by means of the X–Y–Z positioning table relative to the article on the positioning station 34. However, because all the parameters are known in advance, i.e., the particular article portion being imaged at any time and the configuration of the apparatus for providing the illumination, the proper coordinates of the X–Y–Z positioning table are likewise known in advance.

Although it is preferable, owing to its structural simplicity, to use separate and fixedly mounted first mirrors 50 on a rotatable annular support member 48, one alternate arrangement is the use of a single first mirror but which is selectively adjustable in its tilt angle. Thus, light beams of different angles of elevation can be provided by using just a single "first" mirror along with means for controlling the tilt thereof.

Another arrangement is the use of a large number of small mirrors covering substantially the entire inside surface of the annular member 48. Indeed, using known technology, the entire inside surface of the member 48 can be micromachined (to an exceptionally smooth surface), plated and polished to provide a continuous mirror surface of continuously varying tilt around the member inner surface. Because of the continuously varying tilt, the mirror surface is nowhere flat. Still, suitably faithful reflected images are obtainable using a light beam of very small diameter, e.g., such as is obtainable using a laser beam.

The second 46 of the two mirror assemblies comprises but a single "second" mirror 52 disposed (FIG. 4) within a mirror housing 54 mounted on the apparatus central axis 10 but rotatable relative to the axis. The mirror housing 54 is a generally hollow cylindrical structure in which the second mirror 52 is rigidly mounted facing towards an opening 56 through the housing wall. Details of the mounting and rotation of the housing are provided hereinafter.

Figure 5:
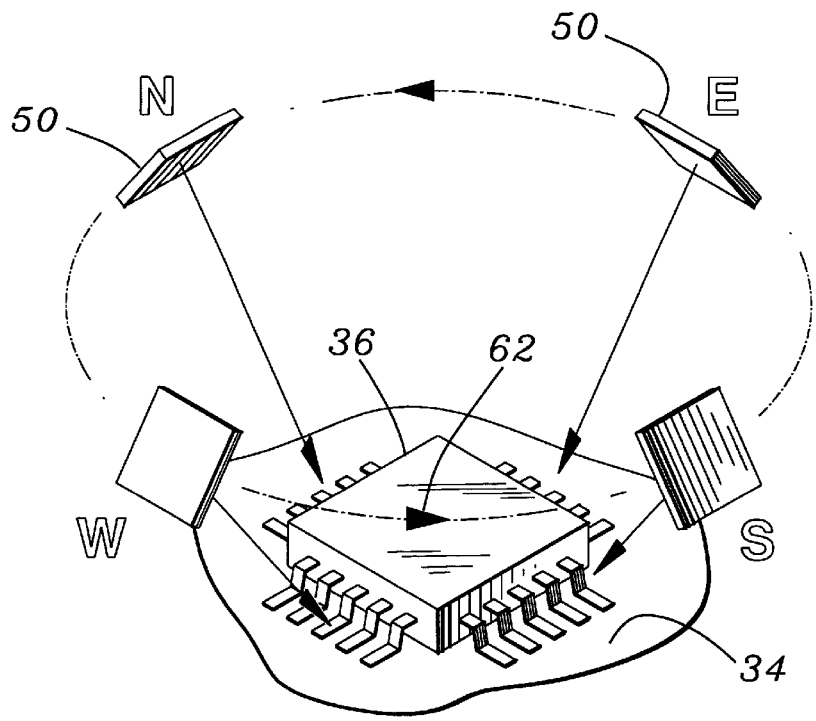
FIG. 5 is a view of an object being illuminated by the apparatus and designating directions of illumination thereof.

The second mirror 52 is fixedly tilted within the housing 54 at an angle of 45 degrees to the central axis 10 whereby light directed onto the mirror 52 from along the central axis 10, for all angular positions of the housing 54 and the mirror 52, is reflected along directions 58 radial to the central axis. The radial directions 58 lie in a radial plane and, assuming the face of a compass lying in the radial plane and centered on the central axis, it is convenient to define the direction of the light reflected from the second mirror in terms of compass directions, e.g., N, E, W and S. Such compass directions are indicated in FIG. 5, but in connection with light reflected from the first mirrors 50 towards an object 36 at the receiving station 34.

Figure 4:
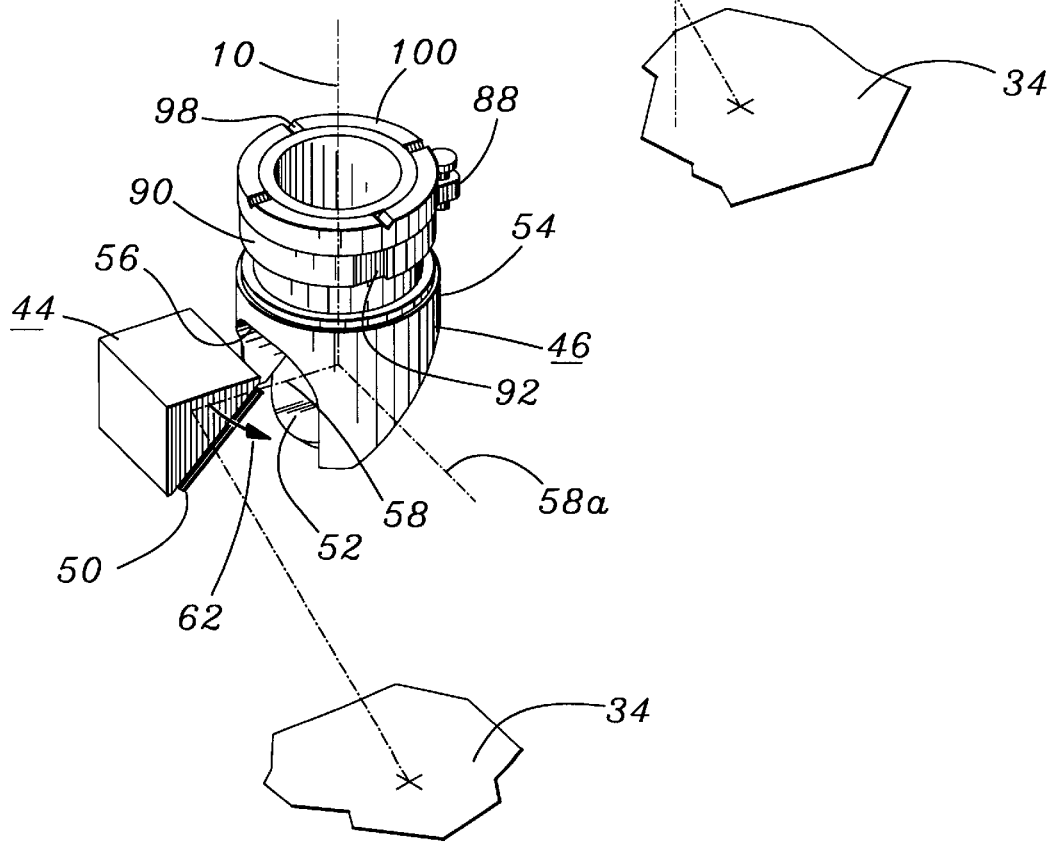

The light incident on the second or "central" mirror 52 reaches the object receiving station 34 via the first mirrors 50. For any selected compass direction of the central mirror, e.g., as illustrated in FIG. 4 and corresponding to the Westerly direction shown in FIG. 5, light downwardly incident on the central mirror 52 from along the central axis 10 is reflected by the mirror 52 in a Westerly direction towards one of the first mirrors 50 selectively disposed in the path of the light from the central mirror and thence onto the receiving station in an Easterly direction. Accordingly, with the mirror system orientation shown in FIG. 4, an article 36 (FIG. 5) on the receiving station 34 is illuminated with light arriving from the West. Additionally, the light arrives at a particular angle of elevation determined by the particular first mirror 50 then positioned in the light path 58 from the central mirror.

As described, the annular support 48 (FIG. 3) is rotatable relative to the central axis 10 independently of the position of the central mirror 52 whereby any one of the three first mirrors 50 can be successively disposed in the path 58 of light from the central mirror. Accordingly, the article being inspected can be illuminated with light at three different angles of elevation, but (in the present example) always from the same Westerly direction. Which particular angle of elevation is selected is a function of the article under inspection. For example, while light arriving from the West may best illuminate features on one side of an article, different angles of elevation of illumination may be required for avoiding shadowing of a second feature by a brightly illuminated first feature.

The direction of illumination of an article is changed by rotating the mirror housing 54, hence the central mirror 52 therein, about the central axis 10. In the presently described condition, for changing the direction of light reflected from the mirror 52 from a Westerly to, for example, a Southerly direction, the central mirror 52 is rotated 90 degrees in the direction of the arrow 62 in FIG. 4. Then, with the light from the central mirror 52 being reflected in a Southerly direction, e.g., along the direction 58a shown in FIG. 4, by disposing a selected one of the first mirrors 50 in the central mirror light path, the light is directed onto the receiving station 34 (FIG. 5) from a South to a North direction and at an angle of elevation determined by the particular first mirror 50 being employed at any time.

Accordingly, an article being inspected can be illuminated by light from any direction and at any angle of elevation. Then, while the article is so illuminated, an image of the article is captured by the camera.

Regardless how illuminated, the illuminating light is back scattered or reflected generally randomly and generally in all directions. Some of the reflected light retraces the path of the illuminating light, i.e., to the first mirror 50 presently in the path of light from the central mirror, thence, to the central mirror 52 and thence upwardly along the central axis 10. Significantly, only the light which identically retraces the illuminating light is reflected upwardly along the central axis. Some of this upwardly reflected light passes through the beam splitter 20 and, after being focused in the lens system 18 (FIG. 1), enters the light aperture 16 of the TV camera 14. Accordingly, the article being inspected is imaged precisely as if it were being viewed along the direction of its illumination.

However, because the light path from the central mirror 52 to the article being inspected can be changed both in direction and angle of elevation, the article being inspected can likewise be imaged from any of the selected directions and angles of elevation. Additionally, except for indexing movements of the X–Y–Z positioning table (or the receiving station 34) for providing precise aiming of the reflected light beams and sharp focusing of the captured images, the multi-directional viewing of the article under inspection is obtained with a basically stationary imaging system. Rather, the different direction viewings of the article are obtained by selective angular indexing of the several mirrors of the mirror system 32. Such mirror systems, however, can be of quite simple construction (as hereinafter described), hence can be both relatively inexpensive and of small mass. Small mass is desirable both for not requiring a large and expensive X–Y–Z positioning table as well as requiring little force for rotating the various mirror assemblies for changing the viewing directions. Accordingly, the viewing direction selections can be made rapidly for a high rate of operation of the apparatus.

If particularly large articles are being inspected, fine aiming and image focusing may not be required, thereby eliminating the need for the X–Y–Z positioning table. In such case, the only movements required for multi-directional viewing of a stationary article by a fully stationary imaging device are the mirror system movements for selecting the various viewing directions.

As described, the first mirror assembly 44 (FIG. 3), comprising three "first" mirrors 50 mounted on an annular support member 48, is rotatable independently of the rotatable second mirror assembly 46. Most conveniently, as now described, both mirror assemblies 44 and 46 are rotated, either independently or in fixed angular relationship, by a single bidirectional indexable motor 66 shown in FIG. 2.

Figure 6:
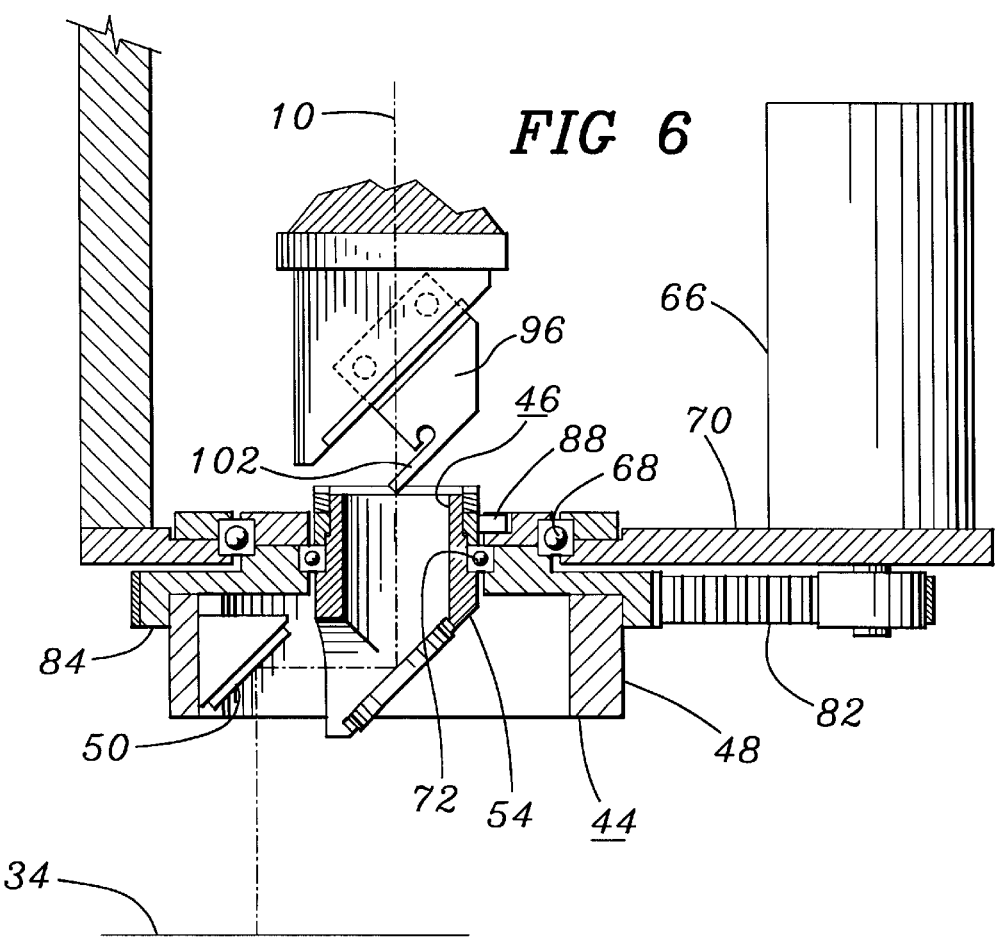
FIG. 6 is a cross-sectional view of a portion of the apparatus including the mirror assemblies thereof.

As shown in FIGS. 2 and 6, both mirror assemblies 44 and 46 are mounted in concentric relationship, with the assembly 44 being rotatably suspended by a bearing 68 from a fixed support member 70, and the assembly 46 being rotatably suspended by a bearing 72 from and within the assembly 44. The two assemblies 44 and 46 are thus held fixedly in place in three dimensions relative to the apparatus central axis 10 (and concentric therewith) but are rotatable about the axis 10.

Rotation is provided by the aforementioned motor 66 which is coupled directly to, and only directly to, the annular support member 48 by means of a timing belt 82 engaged around a timing pulley 84 rigidly secured around the support member 48. The motor 66 thus directly rotates the support member 48 in either direction for proper angular positioning of the "first" mirrors 50 mounted thereon. The motor 66 also rotates the second mirror assembly 46 indirectly via the first mirror assembly 44 as follows.

Figure 7:
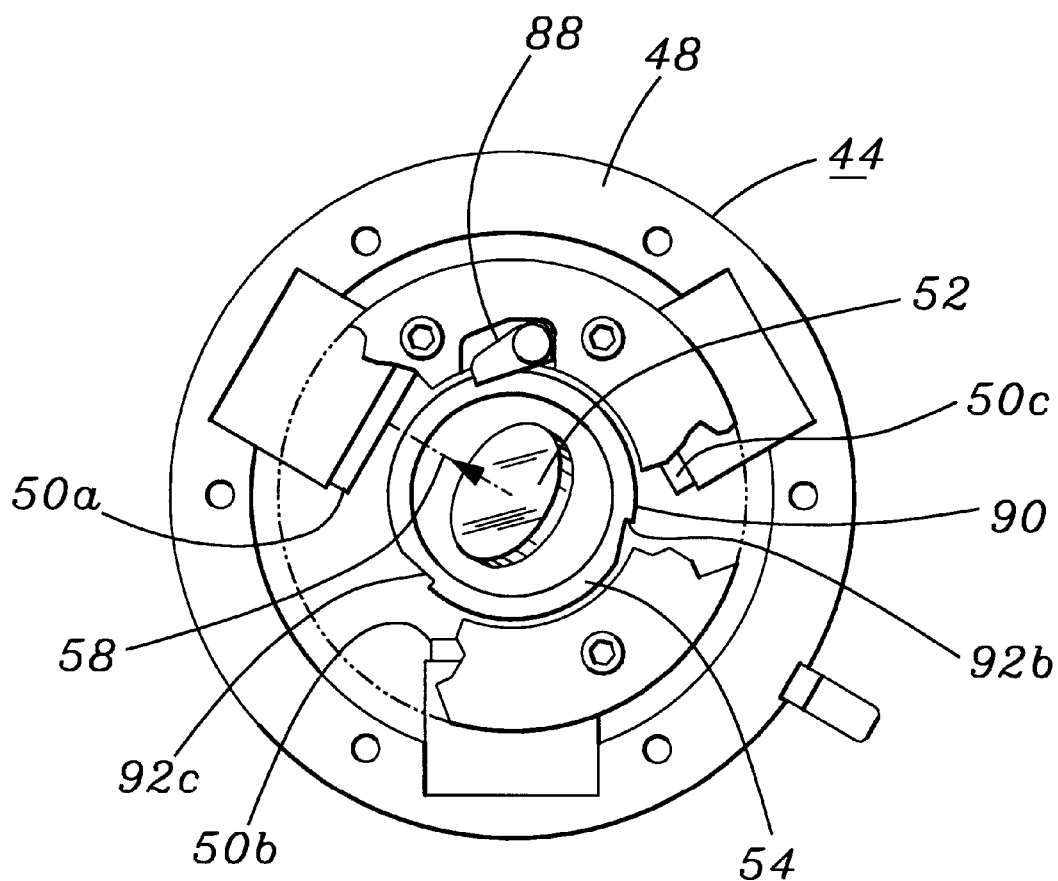
FIG. 7 is a plan view of a portion of the apparatus shown in FIG. 6.

As shown in FIGS. 4, 6, and 7, mounted on the annular support member 48 of the first mirror assembly 44 is a pawl 88 spring biased to project radially inwardly against a circular outer surface 90 of the second assembly housing 54. The housing outer surface 90 contains (in this embodiment) three rachet notches 92 (a, b, and c) for engagement by the spring biased pawl 88. When the annular support member 48 rotates in the clockwise direction as viewed in FIG. 7, the pawl 88 simply slides along the housing surface 90 and over the rachet notches 92. Conversely, when the support member 48 rotates in the counterclockwise direction, the pawl 88 snaps into the first rachet notch 92 it encounters, thus mechanically locking the rotating support member 48 to the housing 54 and causing rotation of the housing 54 in now fixed angular relationship with the support member 48.

In FIG. 7, the reflecting surface of the central mirror 52 disposed within the housing 54 is facing towards a first mirror 50a. Assuming, for purpose of discussion, that the pawl 88 shown in FIG. 7 in locking relationship with the housing 54 is positioned along the North axis and the first mirror 50a is disposed at the North-West position. Accordingly, light reflected from the central mirror 52 is directed onto the object receiving station from the North-West direction (FIG. 5) and at an angle of elevation determined by the tilt angle of the mirror 50a (e.g., 35 degrees).

If the annular support member 48 is then rotated by the motor 66, e.g., 45 degrees in the counterclockwise direction, the mirror 50a will be rotated to a due West position, and the housing 54 and the central mirror 52 therewithin will be similarly rotated 45 degrees counterclockwise. The mirror 50a will remain in the path of reflected light from the central mirror 52, hence the light directed onto the receiving station will now be from the West, but at the same angle of elevation (i.e., 35 degrees in this example).

By continuing the rotation of the support member 48 in the counterclockwise direction (with the housing mirror 54 locked to the support member 48), the light beam from the central mirror 52 will thus be directed onto the receiving station from a continually changing direction but at a constant angle of elevation. Images of an article being inspected can thus be captured from all directions around the periphery of the work station.

Conversely, by rotating the support member 48 in the clockwise direction, e.g., from the position shown in FIG. 7, the housing 54 remains fixed in place (owing to the pawl 88 sliding out of the ratchet notch 92 in which it was disposed), and the stationary central mirror 52 continues to reflect light in the North-West direction. The clockwise rotation of the support member 48 causes the mirror 50a previously disposed in the path 58 of light from the central mirror 52 to rotate out of the central mirror light path. If, for example, the pawl 88 is then caused to snap into the ratchet notch 92b at the South-East position (120 degrees from the North position), the mirror 50b previously (FIG. 7) at the due South position will be rotated to the North-West position and directly into the path 58 of light from the central mirror 52.

As the mirror system 32 is so reconfigured, light from the central mirror is still directed onto the receiving station from the North-West direction, but at some other angle of elevation (e.g., 26 degrees) corresponding to the angle of tilt of the mirror 50b.

By continuing the rotation of the support member 48 in the clockwise direction, the third first mirror 50c (e.g., at 45 degree tilt) will eventually be disposed in the North-West position and in the path of light from the central mirror. Then, the light will be directed vertically downwardly onto the receiving station. With such vertically directed light, the illuminating light has no compass direction of arrival, and the only effect of the angular position of the central mirror is to determine the location of the light spot on the receiving station surface 34.

As previously mentioned, during clockwise rotation of the support member 48, the pawl 88 slides over the housing surface 90 and slides over the ratchet notches 92. To engage the pawl 88 in a selected notch 92, the clockwise rotation is continued until the pawl 88 has passed the selected notch 92 by a small distance, at which time the direction of rotation of the support member is reversed just far enough for the pawl to snap into place in the selected notch 92.

For removing the pawl 88 from within a notch 92 and causing rotation of the support member 48 independently of the central mirror 52, the support member is caused, as previously described, to rotate (FIG. 7) in the clockwise direction. For preventing any rotation of the mirror housing 54 during such clockwise rotation of the support member 48, a latching mechanism 96 (FIG. 6) is provided similar in function and operation to the pawl 88-notch 92 mechanism previously described.

Thus V-notches 98 (FIG. 4) are provided on the upper surface 100 of the cylindrical wall of the central mirror housing 54. The location of each notch corresponds to a preselected compass direction of the central mirror 52. Cooperating with the notches 98 is a stiff but resilient elongated member 102, e.g., of plastic, fixedly mounted in place relative to the mirror housing 54 and pressing, at a fixed angle, against the upper surface 100. Thus, functioning similarly to the previously described pawl 88, the stiff member 102 slides over the housing surface 100 during desired counterclockwise (FIG. 7) rotation of the mirror housing 54, but snaps into a V-notch 98 for preventing clockwise rotation of the housing.

To the extent so far described, the apparatus uses illuminating light from the light source 26 (FIG. 1). While any number of different light sources can be used, a convenient arrangement is the use of a cable 110 comprising a plurality of light fibers. At one end of the cable is a light source, e.g., the aforementioned quartz halogen bulb of known type. Ends of the fibers of the cable are disposed adjacent to the bulb and, using a known lens system, light is directed into the fiber ends and thence through the various fibers. At the cable end shown in FIG. 1, the light exits the fibers and, passing through a lens 28, is collected into a circular converging cone of light directed towards the beam splitter 20. Some of the light is reflected directly downwardly by the beam splitter 20 along the apparatus central axis 10 and thence onto the central mirror 52. In general, the light reaching the receiving station also comprises a circular cone of light. A reason for the use of a light transmitting optical fiber system is that the light source itself, e.g., the halogen bulb and its support and cooling system, can be mounted remotely from the illuminating apparatus and not on it. This avoids undesirable weight loading of the X–Y–Z positioning table and corresponding slower operating speed.

As mentioned, a quartz halogen bulb generates light in the visible and infrared frequency range. Preferably, when using optical fibers to transmit the light, a filter is used to block the infrared spectrum from the fibers for preventing excessive heating of the fibers.

In some instances, particularly when an article is being viewed directly downwardly, i.e., with an angle of elevation of zero degrees (such as provided using the first mirror 50c of 45 degree tilt angle), it is found that clearer imaging is obtained using a diffused lighting. This is accomplished by means of an alternative light source 42 shown in FIGS. 1 and 2.

The light source 42 is of known type known as a "ring-light". Typically, although other arrangements are known and usable, a plurality of light transmitting fibers (not shown) terminate around a circle on the inside surface of an annular support 116. The fibers point downwardly and the rays from adjacent fibers merge to generate a light spot on the receiving station formed from generally non-parallel light rays. Again, in this embodiment, a quartz halogen bulb is used to generate the light.

When the ring light is being used, as shown in phantom in FIG. 1, the ring-light is disposed beneath the mirror system 32, and the light from the ring-light 42 shines directly onto the article being inspected. The mirror system 32 is thus not used for illumination of the article (the first light source 26 generally being turned off), but the mirror system is used for directing light reflected from the article being inspected to the camera 14. To this end, one of the first mirrors 50 is disposed in the light path from the central mirror, and some of the light reflected from the article illuminated by the ring-light 42 reaches the so disposed first mirror and is reflected to the central mirror for reflection along the central axis 10 to the camera. While the camera thus views the article along the direction and angle of elevation established by the respective positions of the central mirror 52 and the first mirror 50 aligned therewith, typically, the 45 degree tilted first mirror 50 is used in combination with the diffuse light source 42 to obtain a direct downward viewing of the object.

Figure 3:
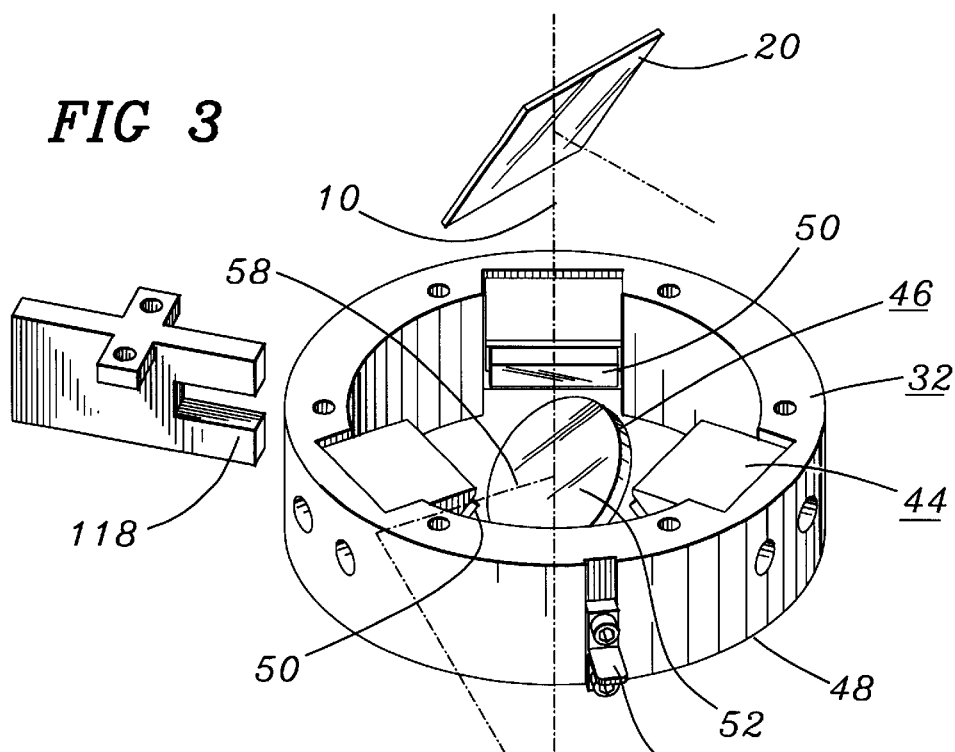
FIGS. 3 and 4 are perspective views of portions of the mirror assemblies used in the apparatus.

Shown in FIG. 3 is a simple arrangement for establishing a preselected angular orientation of the annular support member 48 at the start of operation of the apparatus. A sensor 118, e.g., a proximity sensor, is disposed at a fixed location on the apparatus for detecting the arrival, at the sensor, of a small metal tab 120 mounted on the member 48 for rotation therewith. Starting from such known sensor position, the angular orientation of the support member is readily monitored and controlled using a known servo motor for the driving motor 66 (FIGS. 2 and 6) with encoder feedback, e.g., markings spaced around the periphery of the support member 48 and fixed location optical means for counting the markings as they pass the optical means.

Alternatively, although presently less preferred, the driving motor 66 can be a known "stepper motor" which, from a known starting angular position, can precisely angularly position the support member 48 without positional feedback.

What is claimed is:

1. An apparatus for illuminating an object disposed at an object receiving station by light arriving along a light path from a first light source, said apparatus comprising a first mirror for receipt of light from said light source from along a first axis and for reflecting the light along a second axis onto a second mirror for reflecting the light arriving from said first mirror along a third axis onto said object at a first preselected angle of elevation, means for rotating said first mirror around said first axis for changing the direction of said second axis, means for changing said angle of elevation, and means for moving said second mirror in and out of correspondence with rotation of said first mirror for maintaining said second mirror respectively in and out of the light path from said first mirror.

2. An apparatus according to claim 1 wherein said means for moving said second mirror includes a support member mounted for rotation around said first axis, said second mirror being mounted on said support member, and further including a third mirror mounted on said support member disposable in the path of light from said first mirror in replacement of said second mirror for reflecting light arriving from said first mirror at a second preselected angle of elevation different from said first angle of elevation.

3. An apparatus for illuminating and imaging an object disposed at an object receiving station by light arriving along a light path from a first light source, said apparatus comprising a first mirror for receipt of light from said light source from along a first axis and for reflecting the light along a second axis onto a second mirror for reflecting the light arriving from said first mirror along a third axis onto said object at a first preselected angle of elevation, means for rotating said first mirror around said first axis for changing the direction of said second axis, means for changing said angle of elevation, and an imaging device for forming an image of said object being illuminated by means of light reflected from the illuminated object and reaching the imaging device along a light path including said first, second and third axes.

4. An apparatus according to claim 3 including a second light source for illuminating said object along paths of light independent of said first and second axes.

5. A method of illuminating an object including the steps of establishing a continuous first path of light from a first light source towards the object, said path including a first portion extending in a first direction and a second portion forming a first angle with said first direction and directed towards the object at a first angle of elevation, independently changing the direction of said first portion and the angle of said second portion relative to said first portion, illuminating the object from a second source of illumination along a light path independent of said first portion of said first light path, and capturing an image of the illuminated object by means of light reflected from the object and traveling along said first and second portions of said first light path.

6. A method of illuminating an object including the steps of establishing a continuous first path of light from a light source towards the object, said path including a first portion extending along a first axis, a second portion perpendicular to said first axis, and a third portion forming a first angle with said second portion and directed towards the object at a first angle of elevation, independently rotating said second portion around said first axis and changing said first angle of elevation, and directing light from said light source along said path of light whereby, dependent upon the direction of said second portion and the angle of said second portion with said third portion, the object is illuminated at a preselected one of a plurality of different directions and at one of a plurality of different angles of elevation.

7. An apparatus for illuminating and imaging an object disposed at an object receiving station comprising a light source for illuminating the object by light simultaneously arriving at the object from multiple directions, an imaging device for capturing light traveling along a first axis, a first mirror for receipt of light from along a second axis and for reflecting the received light along said first axis to said imaging device, a second mirror for receipt of light scattered from said object and reaching said second mirror along a third axis, said second mirror being aimed towards said first mirror along said second axis for reflecting the received light to said first mirror, and means for moving said second mirror relative to the object for changing the orientation of said third axis relative to the object while maintaining said second mirror aimed towards said first mirror.

8. A method according to claim 6 wherein the steps of rotating and changing are done while said light source remains stationary.

9. A method of illuminating and imaging an object including establishing a continuous first path of light from the object to an imaging device, said first path including a first portion extending from said imaging device along a first axis, a second portion perpendicular to said first axis, and a third portion forming a first angle with said second portion and directed towards the object at a first angle of elevation, illuminating the object from a source of illumination along a second light path independent of said first and second portions of said first light path, independently changing the direction of said second portion and said first angle of elevation, and capturing an image of the illuminated object by means of light reflected from the object and traveling along said first, second and third portions of said first light path.

* * * * *